United States Patent [19]

Kasprzyk et al.

[11] Patent Number: 5,114,423
[45] Date of Patent: May 19, 1992

[54] DILATATION CATHETER ASSEMBLY WITH HEATED BALLOON

[75] Inventors: Daniel J. Kasprzyk, Sunnyvale; Jean C. Orth, San Jose; John W. Gaiser, Mountain View; Russell A. Houser, Pleasanton, all of Calif.

[73] Assignee: Advanced Cardiovascular Systems, Inc., Santa Clara, Calif.

[21] Appl. No.: 521,337

[22] Filed: May 9, 1990

Related U.S. Application Data

[63] Continuation-in-part of Ser. No. 351,777, May 15, 1989.

[51] Int. Cl.⁵ .................................. A61M 29/00
[52] U.S. Cl. .......................... 606/27; 606/28; 606/191; 606/192; 606/194; 604/95; 604/96
[58] Field of Search ........... 606/191, 192, 194, 27–28, 606/30–33, 7, 159; 604/98, 96

[56] References Cited

U.S. PATENT DOCUMENTS

| | | | |
|---|---|---|---|
| 4,552,127 | 11/1985 | Schiff | 606/192 X |
| 4,641,649 | 2/1987 | Wallinsky et al. | 606/33 |
| 4,643,186 | 2/1987 | Rosen et al. | 606/159 X |
| 4,654,024 | 3/1987 | Crittenden et al. | 606/31 X |
| 4,672,962 | 6/1987 | Hershenson | 606/28 |
| 4,799,479 | 1/1989 | Spears | 606/7 X |
| 4,808,164 | 2/1989 | Hess | 606/194 X |

Primary Examiner—Robert A. Hafer
Assistant Examiner—Kerry Owens
Attorney, Agent, or Firm—Fulwider, Patton, Lee & Utecht

[57] ABSTRACT

A balloon dilatation catheter having heating elements raise the temperature of the working surface of the balloon while the balloon is being inflated during an angioplasty procedure. In one embodiment, the balloon is provided with a thin electrically conductive layer in heat transfer relationship therewith preferably on the interior surface of the balloon. Electrical power at radio frequencies is preferred and a coaxial cable is employed to deliver such power to a conductive layer for heating the balloon. In another embodiment, the ballon itself is formed of electrically conductive material. A perfusion lumen may be provided through the balloon with one or more proximal inlet ports and one or more distal discharge ports in fluid communication with the lumen to allow blood to pass through the balloon when it is inflated during angioplasty procedures. This faciltiates the flow of oxygenated blood distally of the catheter when the balloon is inflated thus allowing for extended balloon inflations, e.g., up to 30 minutes or more. The catheter assembly may also be employed to treat myocardial infarction by dilating thrombotic occlusions.

5 Claims, 5 Drawing Sheets

Fig. 12 ns filed May 15, 1989.

DILATATION CATHETER ASSEMBLY WITH HEATED BALLOON

RELATED APPLICATIONS

This application is a continuation in part of U.S. application Ser. No. 351,777 filed May 15, 1989.

BACKGROUND OF THE INVENTION

This invention generally relates to a dilatation catheter suitable for angioplasty procedures which has a dilatation balloon with heated working surface and particularly to such a catheter which can perfuse blood distally of the balloon during the inflation thereof.

In typical percutaneous transluminal coronary angioplasty (PTCA) procedures, a guiding catheter having a preformed distal tip is percutaneously introduced into the cardiovascular system of a patient through the brachial or femoral arteries and advanced therein until the distal tip thereof is in the ostium of the desired coronary artery. A guidewire and a dilatation catheter having a balloon on the distal end thereof are introduced through the guiding catheter with the guidewire slidably disposed within an inner lumen of the dilatation catheter. The guidewire is first advanced into the patient's coronary vasculature until the distal end thereof crosses the lesion to be dilated and then the dilatation catheter is advanced over the previously introduced guidewire until the dilatation balloon is properly positioned across the lesion. Once in position across the lesion, the flexible, relatively inelastic balloon is inflated to a predetermined size with radiopaque liquid at relatively high pressures (e.g., greater than about 4 atmospheres) to radially compress the atherosclerotic plaque of the lesion against the inside of the artery wall to thereby dilate the lumen of the artery. The balloon is then deflated so that the dilatation catheter can be removed and blood flow resumed through the dilated artery.

Further details of angioplasty procedures and the devices used in such procedures can be found in U.S. Pat. No. 4,323,071 (Simpson-Robert); U.S. Pat. No. 4,332,254 (Lundquist); U.S. Pat. No. 4,439,185 (Lundquist); U.S. Pat. No. 4,168,224 (Enzmann et al.) U.S. Pat. No. 4,516,972 (Samson); U.S. Pat. No. 4,538,622 (Samson et al.); U.S. Pat. No. 4,554,929 (Samson et al.); and U.S. Pat. No. 4,616,652 (Simpson) which are hereby incorporated herein in their entirety.

Steerable dilatation catheters with built-in or fixed guidewires or guiding elements are used with increasing frequency because such catheters generally have smaller deflated profiles than conventional dilatation catheters with movable guidewires or elements with equivalent balloon size. The lower deflated profile of these catheters allows them to cross tighter lesions and to be advanced much deeper into the patient's coronary anatomy. Moreover, the use of steerable low-profile dilatation catheters can shorten the time for the angioplasty procedure because there is no need to first advance a guidewire across a lesion and then slide a conventional dilatation catheter over the previously advanced guidewire to position the balloon thereof across the lesion. Further details of low-profile steerable dilatation catheters may be found in U.S. Pat. No. 4,582,181 (Samson); U.S. Pat. No. 4,619,263 (Frisbie et al.); U.S. Pat. No. 4,641,654 (Samson et al.); and U.S. Pat. No. 4,664,113 (Frisbie et al.) which are hereby incorporated in their entirety by reference thereto.

Recently, efforts have been made to raise the temperature of the stenotic region during the dilation thereof in the belief that such procedures can minimize restenosis and can prevent abrupt reclosure of the artery when the balloon is deflated and removed. See, for example, U.S. Pat. No. 4,799,479 (Spears) and U.S. Pat. No. 4,643,186 (Rosen) Reference is also made to U.S. Pat. No. 4,662,368 (Hussein et al.) and U.S. Pat. No. 4,807,620 (Strul) which disclose catheters with an enlarged heated probe on the distal tip thereof for opening totally occluded arteries.

However, the prior catheters which applied heat to the atheroma had several disadvantages which can limit their usefulness in humans. For example, the direct irradiation employed in some of these devices can cause extensive coagulation of the blood and thermal injury to the tissue which surrounds the catheter at the treatment site. Moreover, frequently the operator's lack of knowledge of the temperature of the heating element can preclude effective moderation of the thermal treatment level. Additionally, non-uniform heating of the treatment area can create uncertainty whether the treatment area is receiving too much or too little heat. Clinically, these disadvantages have in some cases produced extreme pain, vessel reocclusion or aneurysm. None of the prior devices allowed for long-term dilations at elevated temperature.

What has been needed and heretofore unavailable is a balloon dilatation catheter assembly of simple construction and powered by inexpensive equipment which can quickly and uniformly heat up the atheroma during or following the dilatation thereof and preferably which can also perfuse oxygenated blood distally of the catheter when the balloon is inflated to facilitate effective long-term dilations. The present invention satisfies that need.

SUMMARY OF THE INVENTION

This invention is directed to an improved balloon dilatation catheter which has means for heating the balloon during angioplasty procedures which may also have means to perfuse blood distally of the catheter when the balloon is inflated to facilitate long-term dilations.

The dilatation catheter in accordance with the invention includes an elongated tubular body with an inflatable balloon proximally adjacent the distal end thereof with an inner lumen extending within the tubular body to direct inflation fluid therethrough to the interior of the balloon. A thin conductive layer is provided which is in a radial heat transfer relationship with the working surface (i.e., the outer cylindrical surface) of the balloon and which is coextensive with a substantial portion (i.e., more than 30%, preferably all) of said working surface. In an alternative embodiment, part or all of the balloon itself is formed of conductive material. Electrical conducting means, such as deposited metal layers, foils, or wires may extend longitudinally through the elongated tubular body to electrically connect the thin conductive layer associated with the working surface of the balloon or the conductive balloon to an exterior electrical power source.

The thin electrically conductive layer on the inner surface of the balloon is preferably formed of an electrically conductive polymer, such as polyethylene based polymer, which has incorporated therein conductive metal particles or powder such as silver or gold or other conductive materials such as carbon fibers. Additionally, other metals such as tantalum can be incorporated into the conductive layer to control the resistive heating thereof and to also facilitate fluoroscopic observation of the balloon during the angioplasty procedures.

Electrical power within the radio frequency range is preferred for the rapid and effective heating of the thin conductive layer in a heat transfer relationship with the working surface of the balloon. Such radio frequency power may be effectively delivered to the thin conductive layer by means of a coaxial cable which extends from the proximal end of the catheter through an inner lumen of the tubular body. The coaxial cable generally includes an outer layer of electrically conductive material (e.g., copper, aluminum, silver or gold or alloys thereof) an intermediate layer of dielectric material, such as polytetrafluoroethylene (Teflon®) or polyimide, and an inner layer or core formed from electrically conductive materials, such as those described above. The inner conductive layer may be supported by an inner tubular member formed of high-strength plastic material, such as polyimide, which is longitudinally flexible but diametrically relatively rigid. In some embodiments, the inner conductive member may be a solid wire or rod.

In a presently preferred embodiment, the dilatation catheter is provided with a lumen passing through the interior of the balloon with inlet ports proximal to the balloon and discharge ports distal to the balloon to perfuse oxygenated blood to tissue distal to the catheter when the balloon is inflated during angioplasty procedures to permit extended dilatation periods. Long-term dilations of up to 30 minutes or more with a heated balloon allow for lower effective balloon temperatures. The ability of this embodiment of the invention to perfuse oxygenated blood distal to the inflated balloon makes the catheter assembly suitable for dilating a thrombus and forming an interior passageway there through with little chance of emboli forming which may become disengaged from the main body of the thrombus and drift distally from the blockage.

While utilization of a thin conductive polymer layer to raise the temperature of the working surfaces of the dilatation balloon is a presently preferred embodiment, alternatives can be used. For example, the thin conductive polymer layer may be replaced by a metallic layer, such as gold, silver, copper, titanium, nichrome, and the like. The conductive layer may be on the interior or exterior surface of the balloon or on the exterior surface of the inner tubular member within the interior of the balloon. In the latter instance, the conductor can be wrapped around or otherwise secured to the exterior portion of the inner tubular member disposed within the interior of the balloon. However, if the conductor is on the exterior surface of the balloon, an insulating coating would be required on the metal surface to minimize current flow into the surrounding tissue when the balloon is inflated and heated. Additionally, the balloon member or the inner tubular member passing through the interior of the balloon may be formed of conductive material, e.g., a conductive carbon loaded plastic such as polyethylene terephthalate. However, as with metallic layers, a thin non-conductive layer is provided on the exterior of the balloon to minimize current flow into surrounding tissue. A particularly attractive material is conductive carbon fibers which have temperature limiting characteristics, i.e. as the current rises, the temperature rises which causes expansion which in turn limits the current.

In some situations it is advantageous to heat only portions of the balloon surface. For example, occasionally atherosclerotic plaque builds up on only one side of an arterial wall. Heating of the entire circumference of the balloon can injure the portion of the arterial wall which has little or no plaque buildup. By providing separately controlled heating elements only the balloon section adjacent to the plaque would have to be heated to elevated temperatures when the balloon is inflated. The individual heating elements may have separate electrical power sources.

The electrical power supplied to the heat up element or plurality of heat up elements, may be controlled in response to the temperature of the balloon by a suitable feedback control system. The temperature of the outer surface of the balloon is determined directly or indirectly by suitable means and a signal representing the determined value is fed back to a control system which adjusts the output of the power source in response thereto to maintain the desired temperature or other parameter related to the temperature. A simple, inexpensive way to control the electrical power input to the catheter assembly is to calibrate the assembly to heat up to and maintain a desired temperature.

These and other advantages of the invention will become more apparent from the following detailed description of the invention and the attached exemplary drawings.

DETAILED DESCRIPTION OF THE INVENTION

Figure 1:
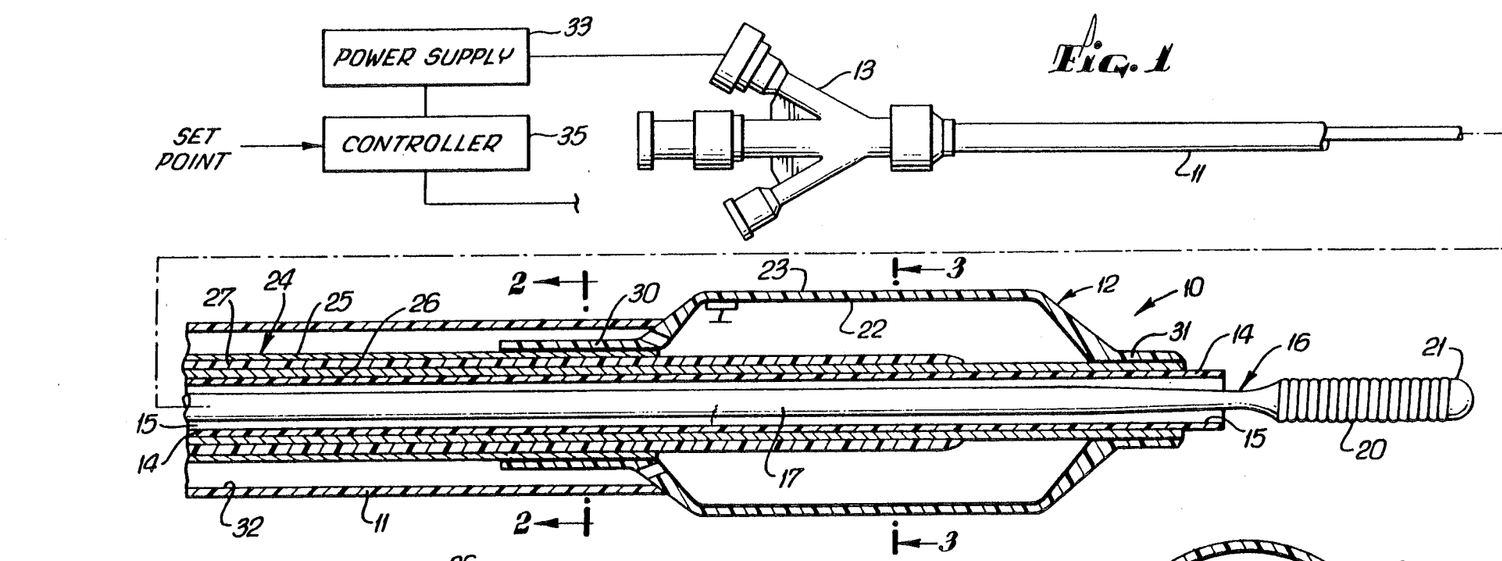
FIG. 1 is an elevational view partially in section of a dilatation catheter embodying features of the invention.
Figure 2:
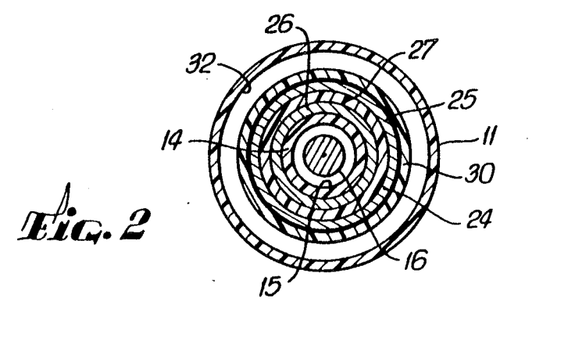
FIG. 2 is a transverse cross-sectional view taken along the lines of 2—2 shown in FIG. 1.
Figure 3:
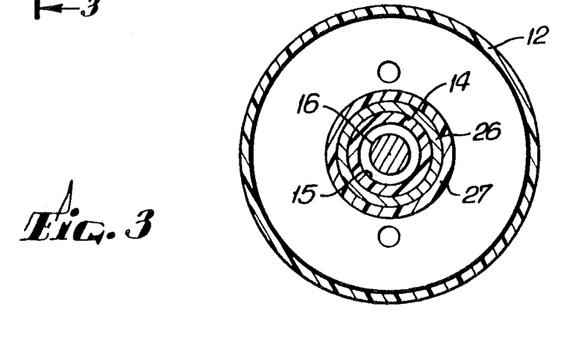
FIG. 3 is a transverse cross-sectional view taken along the lines 3—3 shown in FIG. 1.

Reference is made to FIGS. 1-3 which illustrate a dilatation catheter assembly 10 embodying features of the invention. The catheter assembly 10 generally comprises an outer tubular member 11, an inflatable dilatation balloon 12, and a multi-arm adapter 13 which facilitates directing inflation fluid to the interior of the balloon 12. An inner tubular member 14, preferably formed of nonconducting plastic material, is concentrically disposed within the outer tubular member 11 and has an inner lumen 15 adapted to slidably receive therein a guidewire 16. The guidewire 16 generally comprises an elongated core member 17 and a flexible radiopaque coil 20 on the distal portion thereof. A rounded radiopaque plug 21 is formed on the distal tip of guidewire 16.

The interior surface of the balloon 12 is provided with a thin conductive layer 22 in radial heat transfer relationship therewith, which, when electrical current is passed therethrough, resistively heats up and thereby raises the temperature of the exterior working surface 23 of the balloon 12. Preferably, the entire interior of the working surface of the balloon 12 is coated with the conductive layer 22.

Coaxial cable 24 extends between outer tubular member 11 and inner tubular member 14 and generally comprises an outer conductive layer 25, an inner conductive layer 26 and an annular dielectric layer 27 disposed therebetween. The outer conductive layer 25 is electrically connected to the thin conductive layer 22 at the proximal end or shoulder 30 of the balloon 12 and the inner conductive layer 26 extends through the interior of the balloon 12 and is electrically connected to the thin conductive layer 22 at the distal end or shoulder 31 of balloon 12. Both the outer and inner conductive surfaces 25 and 26 may be coated with a thin insulating layer (not shown) to prevent contact with the inflation medium. An annular passageway 32 extends between the outer tubular member 11 and the outer surface of the coaxial cable 24 to direct inflation fluid from the adapter 13 into the interior of the balloon 12.

The coaxial cable 24 is connected at its proximal end to a suitable electrical power source 33. While such a power source may provide direct current or any suitable frequency of alternating current, in this embodiment the preferred frequency is between about 100 kilohertz and about 100 megahertz. Current frequency in excess of 100 kilohertz is less likely to affect heart muscle contraction and therefore is safer. Typically, the frequency employed is 40 megahertz and the power is about 2 to about 20 watts, preferably about 4 to 12 watts. A suitable radio frequency electrical power source is manufactured by Engineering Research Associates in Tucson, Ariz.

The power source 33 is preferably controlled based directly or indirectly upon the temperature of the balloon 12. In a preferred embodiment, the resistance load of the balloon including the leads thereto is monitored by an ohmmeter (not shown) and the output of the electrical power source is controlled in response thereto. The signal generated by the ohmmeter is compared with a signal representing a desired set point in a controller 35 which provides a control signal to the power source 33 in a conventional feedback control system, as shown schematically in FIG. 1, to control the output thereof. A wide variety of control systems and strategies may be employed.

In the embodiment shown in FIGS. 1-3, the outer tubular member 11 is preferably formed of polyester such as Hytrel, the balloon is formed of a biaxially oriented polyethylene terephthalate, and the inner tubular member 14 is formed of polyimide tubing having a wall thickness of about 0.001 inch. A suitable polyimide tubing is sold by H. V. Technologies in Trenton, Ga. The conductive layer on the interior surface of the balloon is a polyethylene having an electrically conductive metal such as silver or gold incorporated therein to provide the electrically conductive properties. Powdered tantalum can be incorporated into the coating to control the resistive heating of the layer 22 when electrical current passes therethrough. The presently preferred conductive polymer is CC40A polymer coating material sold by the Emerson & Cummings Company.

The conductive layer applied to the interior of the dilatation balloon is preferably formed of a polyethylene based conductive polymer sold under the name of CC40A by the Emerson and Cummings Company which is conductive due to the incorporation therein of silver. To apply the coating, the polymer resin is mixed with suitable solvent, such as toluene, and then applied to coat the interior of the balloon. The balloon with the interior so coated is then placed in an oven at about 90° C. for approximately 2 hours to drive off the solvent and to complete the curing of the polymer material. Coating thicknesses should range from about 0.0002 to about 0.0002 inch (0.0051–0.051 mm) with a typical thickness being about 0.001 inch (0.025 mm). Thereafter, the balloon can be secured to the tubular member in a suitable manner such as by heat shrinking the shoulders thereof to the tubular member of by the use of a suitable adhesive such as a conductive epoxy.

Various modifications can be made to the invention. For example, a perfusion lumen can be utilized separate and distinct from the guidewire lumen as shown in Ser. No. 223,088, filed Jul. 22, 1988, which is incorporated herein in its entirety. Additionally, the balloon may be formed in the tubular member by heating and inflating as described in U.S. Pat. No. 4,323,071 (Simpson-Robert). Other modifications and improvements can be made without departing from the scope thereof.

Teflon ® or polyimide tubing, preferably about 0.006 inch thick, is disposed between the inner and outer conductive layers of the coaxial cable 24 as the dielectric layer.

FIGS. 4-7 illustrates another embodiment of a balloon dilatation catheter with a heated balloon which provides for the perfusion of blood distally of the catheter when the balloon thereof is inflated and heated during an angioplasty procedure. The catheter of this embodiment generally comprises a tubular member 40 having a small inner lumen 41, a large inner lumen 42, and a balloon 43 secured by shoulders 44 and 45 thereof to the tubular member. A plurality of inlet ports 46 in the wall of the tubular member 40 are provided proximal to the balloon 43 and a plurality of discharge ports 47 are provided distal thereto. Both the inlet and discharge ports are in fluid communication with the large lumen 42 which extends through the interior of balloon 43. In this manner, when the balloon 43 is inflated and heated for extended periods of time, blood will flow through the inlet ports 46 into lumen 42 and be discharged through ports 47 to supply oxygenated blood to tissue distal to the catheter.

The small lumen 41 contains electrical conductors 50 and 51 for directing electrical power from a source (not shown) exterior to the catheter to the electrically conductive layer 52 provided on the interior of the balloon 43. The small lumen 41 opens into the interior of the balloon 43 with conductor 50 extending to the proximal end or shoulder 44 of the balloon 43 and conductor 51 extends to the distal end or shoulder 45. Generally, the conductors 50 and 51 are wrapped several times about the tubular member 40 underneath the ends or shoulders of the balloon 43 to contact the conductive layer 52 on the inner surface thereof. While the entire interior of the cylindrically shaped portion (the working surface) of the balloon 43 is preferably coated with conductive layer 52, a patterned layer may be used so that both connections thereto can be at the same end of the balloon in order to control the heating of the balloon in a desired fashion.

Figure 4:
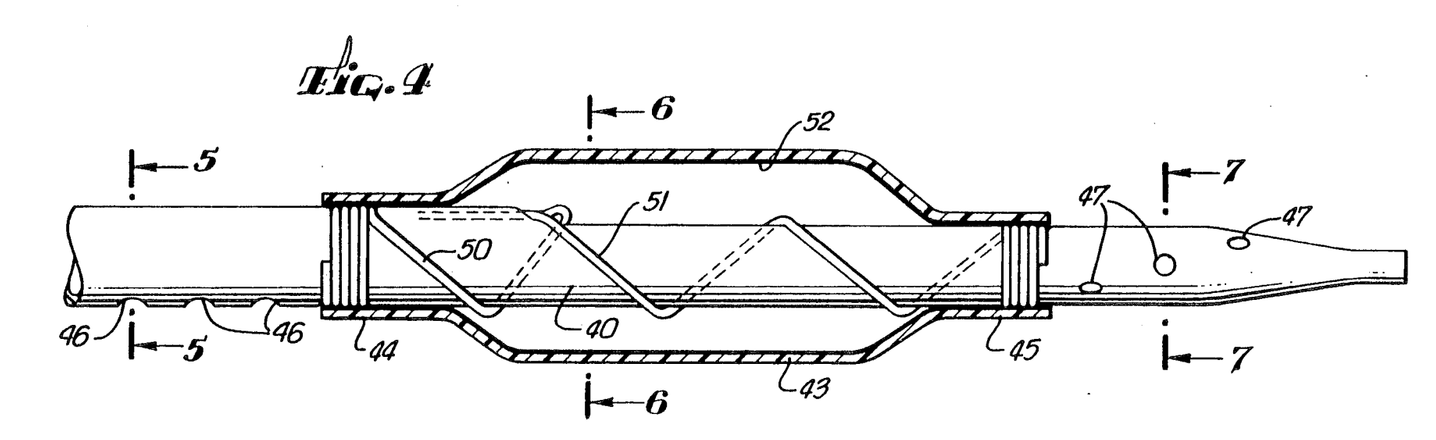
FIG. 4 is an elevational view partially in section of a perfusion dilatation catheter which embodies features of the invention.
Figure 5:
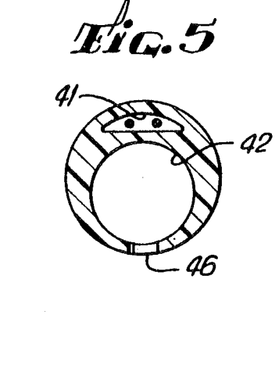
FIG. 5 is a cross-sectional view taken along the lines 5—5 shown in FIG. 4.
Figure 6:
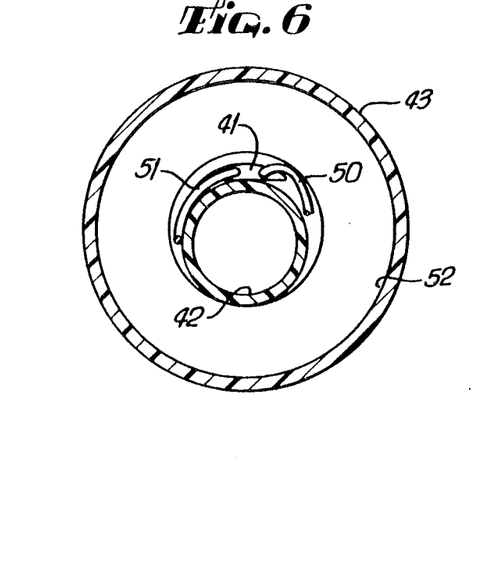
FIG. 6 is a cross-sectional view taken along the lines 6—6 shown in FIG. 4.
Figure 7:
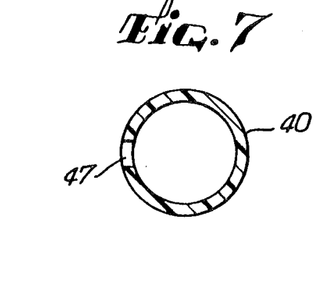
FIG. 7 is a cross-sectional view taken along the lines 7—7 shown in FIG. 4.
Figure 8:
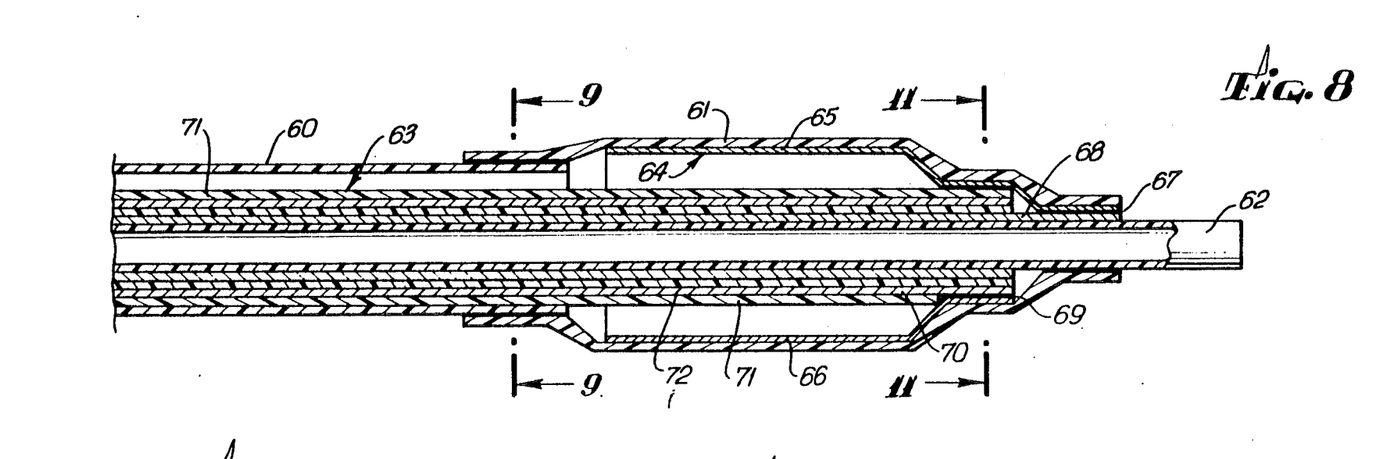
FIG. 8 is a longitudinal view, in section, of an alternative embodiment of a dilatation catheter which embodies features of the invention.
Figure 9:
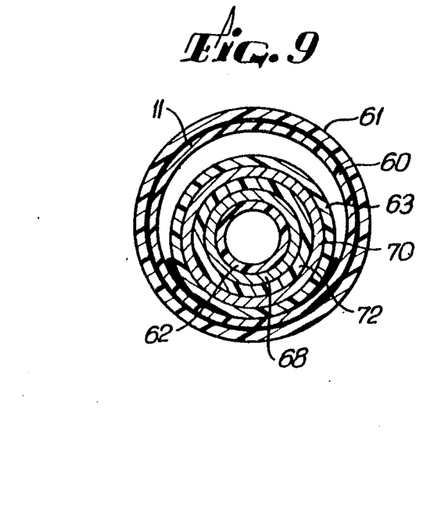
FIG. 9 is a cross-sectional view taken along the line 9—9 shown in FIG. 8.
Figure 10:
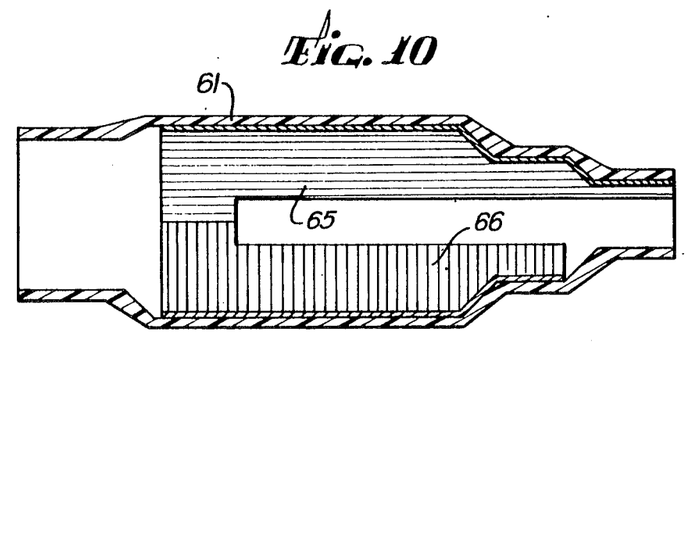
FIG. 10 is a cross-sectional view similar to FIG. 8 with parts removed to illustrate the layer of conductive material on the interior surface of the balloon.
Figure 11:
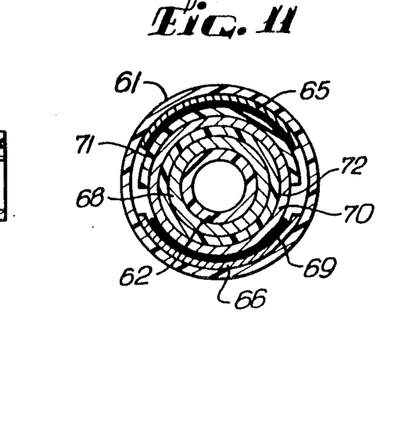
FIG. 11 is a cross-sectional view taken along the line 11—11 shown in FIG. 8.

The passage of electricity through the conductive layer 52 on the interior of the balloon 43 provides sufficient heat to raise the temperature of the exterior working surface 53 of the balloon 43 to the desired levels. In this embodiment, the electrical current may be direct current or current at radio frequencies.

The larger lumen 42 is adapted to receive a guidewire as shown in FIG. 1 to facilitate the advancement of the catheter through the patient's arterial system in a conventional fashion.

FIGS. 8-11 illustrate another embodiment which also has a coaxial cable to transmit electrical power to the heating element of the balloon. The dilatation catheter of this embodiment has an outer tubular member 60 with an inflatable balloon member 61 secured to the distal end thereof and an inner tubular member 62 disposed within the outer tubular member and extending distally through the interior of the balloon. A coaxial cable 63 is disposed about the exterior of inner tubular member 62.

The interior of the balloon is provided with an electrically conductive layer 64 having an upper portion 65 and a lower portion 66. Portions 65 and 66 provide an electrical pathway over the interior of the balloon 61 and allow the ends of the pathway to be electrically connected to coaxial cable 63 at the distal end of the balloon. Upper half 65 is secured by means of electrically conductive adhesive 67 to inner conductive layer 68 of the coaxial cable 63 and the lower half is similarly bonded by electrically conductive adhesive 69 to outer conductive layer 70 of the coaxial cable 63. An outer insulated covering 71 is provided on the exterior of the outer conductive layer 70 and an inner dielectrical layer 72 is provided between the inner and outer conductive layers 68 and 70.

The materials of construction of the prior embodiments are suitable for use in the embodiments shown in FIGS. 8-11.

Figure 12:
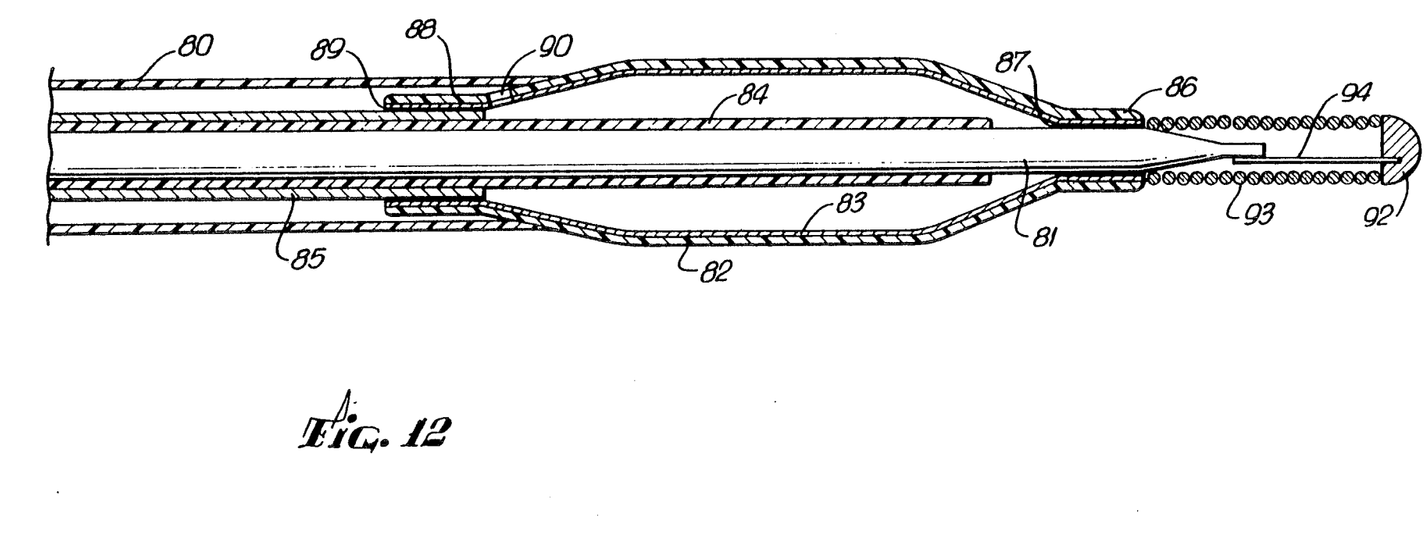
FIG. 12 is a cross-sectional view of a low-profile steerable catheter embodying features of the invention.

FIG. 12 illustrates a low-profile steerable dilatation catheter which embodies features of the invention. In this embodiment, the catheter has an outer tubular member 80, an electrically conductive core member 81 disposed within the outer tubular member, and an inelastic inflatable balloon 82 having an electrically conductive layer 83 on the inner surface thereof. The electrically conductive core member 81 has a non-conductive dielectric layer 84 on the exterior surface thereof which in turn has an electrically conductive layer 85 thereon. Both conductive layer 85 and conductive core member 81 may be provided with an insulating outer layer (not shown) to prevent direct contact with the inflation medium or body fluids.

The portions of the core member 81 immediately adjacent the distal end or shoulder 86 of balloon 82 has both the conductive layer 85 and the dielectric layer 84 removed to facilitate the bonding of the core to the conductive layer 83 on the distal end or shoulder 86 of the balloon 82 by means of electrically conductive adhesive 87. The proximal end or shoulder 88 of balloon 82 is similarly secured by electrically conductive adhesive 89 to the outer conductive layer 85. A plurality of passageways 90 are provided in the tapered section of balloon 82 to allow inflation fluid to pass from the annular lumen 91 into the interior of the balloon.

In this embodiment, the distal end of the core member 81 terminates short of the distal plug 92 on the coil 93 and a shaping ribbon 94 is secured to the distal end of core 81 and extends to the plug 92. Other tip constructions may be employed. For example, the core member 81 can extend to the plug 92.

Torquing means (not shown) are provided on the proximal end of the core member 81 as will be appreciated by those skilled in the art to facilitate the advancement of the catheter through a patient's vasculature. The portion of the core member 81 distal to the connection thereof to the distal end of the balloon 82 is preferably coated with insulating material (not shown) in order to prevent the passage of electrical current into surrounding tissue. Both direct current and current at radio frequencies may be employed to heat up the working surface of the balloon as in the other embodiments.

Another preferred embodiment of the invention is disclosed in FIGS. 13-16. In this embodiment the catheter 100 generally has a catheter body 101 with a dual lumen proximal portion 102 which extends distally from the proximal end thereof to the interior of the balloon 103. The upper lumen 104 of the dual lumen section has a crescent shaped transverse cross-section and directs inflation of fluid to the interior of the balloon 103. A second lumen 105 of the proximal portion 102 has a circular transverse cross-section which is adapted to receive a guidewire 106 therein. The catheter body 101 has a distal section 107 which continues through the interior of the balloon 103 and out the distal end thereof. Perfusion holes 110 are provided in the wall of the proximal portion 102 of the catheter body 101 and fluid communication with the second lumen 105 and perfusion holes 111 are provided in the wall of the distal portion 107 distal to the balloon.

Figure 13:
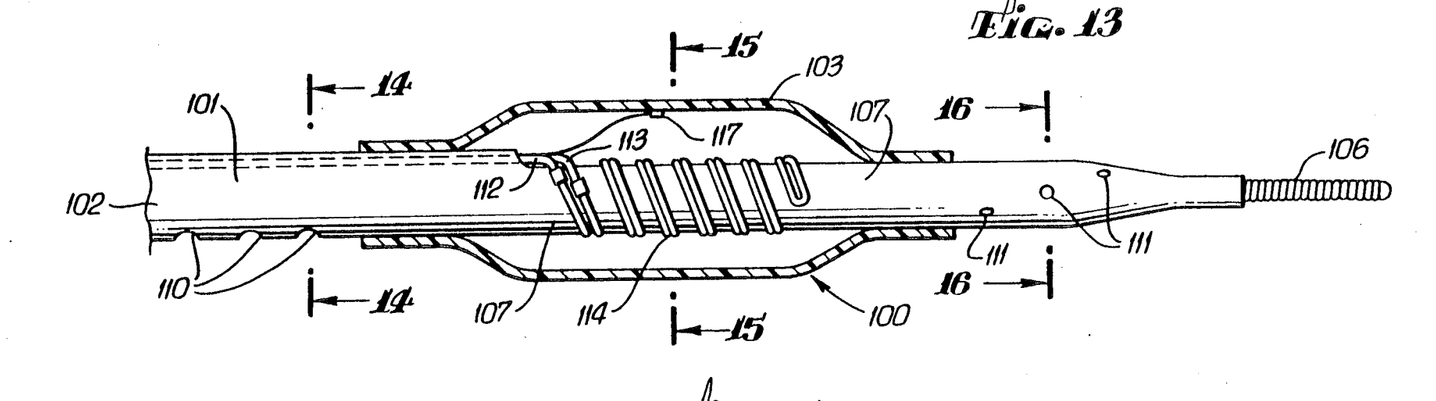
FIG. 13 is an elevational view, partially in section of another embodiment of the invention.
Figure 14:
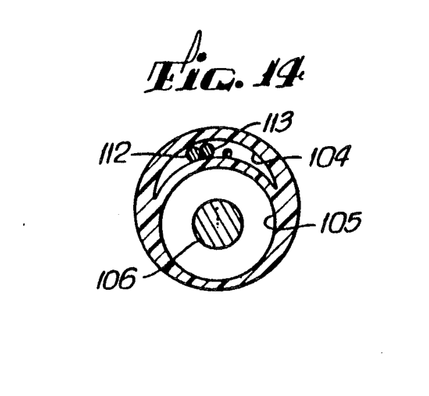
FIG. 14 is a transverse cross-sectional view taken along the lines 14—14 shown in FIG. 13.
Figure 15:
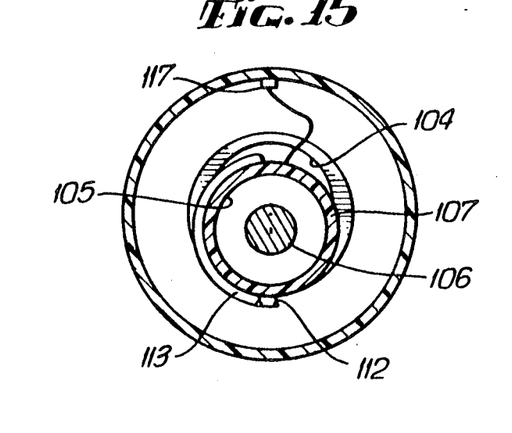
FIG. 15 is a transverse cross-sectional view taken along the lines 15—15 shown in FIG. 13.
Figure 16:
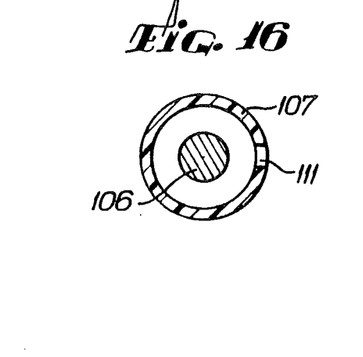
FIG. 16 is transverse cross-sectional view taken along the lines 16—16 shown in FIG. 13.

The balloon 103 is preferably relatively inelastic and may be formed of suitable materials such as polyethylene, polyethylene terephthalate and other suitable materials. It is secured to the catheter body 102 by both the proximal and distal ends thereof by suitable means such as adhesive or solvent bonding.

Lead or bus wires 112 and 113 are provided within the first inflation lumen 104. The proximal ends thereof (not shown) extend out the proximal end of the catheter 100 and are suitably connected to a power source (not shown in this figure) the distal ends are electrically connected (e.g., by soldering) to heating element 114 which is coiled about the distal portion 107 of the catheter body 101 which extends through the interior of the balloon 103. The heating element may be a loop of resistive load made of Monel, nichrome or other suitable alloy wire and is preferably bonded to the underlying distal portion 107 by suitable adhesives such as cyanoacrylate or a UV cured epoxy. The heating element may be formed at least partly of temperature limiting fibrous carbon material such as Celion G30-400 carbon fiber from the BASF Corporation. The heating element may be incorporated into the wall of the distal portion 107 of the catheter body 101 within the balloon 103 or the distal portion itself may be formed of electrically resistive material to function as the heating element.

The proximal portion 102 and the distal portion 107 of the catheter body 101 are preferably formed of separate extrusions of polyester (e.g., Hytrel) butt joined by suitable means such as heat and pressure or an adhesive. The distal portion 107 within the interior of the balloon 103 is preferably thick walled (e.g., 0.005 inch), formed of high strength materials or reinforced in some manner to prevent collapse during the time the balloon 103 is inflated, but a thinner more flexible portion thereof extends under the junction with the distal end of the balloon to minimize vessel trauma when advancing the catheter through a patient's coronary anatomy.

At least five and preferably about 10 proximal perfusion holes 110 are provided in the wall of the proximal portion 102 of the catheter body 101 and at least 2, preferably 4 distal perfusion holes 111 are provided in the wall of the distal portion 107.

An electrical power source (not shown) preferably operates at a frequency of about 100 to about 750 kilohertz (e.g., 250 KHZ) with a maximum power availability of about 20 watts. Preferably a battery-powered source (e.g., 12 volts) is used for maximum patient isolation and protection. The power source may be controlled by a conventional analog feedback circuit which has one or more temperature sensing devices 117 such as thermocouples, thermistors and the like suitably secured by an adhesive to the inner surface of the balloon 103 or to the heating coil 114. When multiple temperature sensors are employed either the maximum temperature sensed or an average temperature sensed by all of the temperature sensors thermocouples may be employed for control purposes.

In use the catheter 100 is advanced preferably over a guidewire 106 until the balloon crosses the stenotic region of a patient's arterial system which is to be treated. The balloon 103 is inflated by means of an inflation liquid which passes through inflation lumen 104 so as to press the working surface of the balloon against the atherosclerotic plaque which lines the stenotic region.

Electrical current about 250 KHz is directed through leads 112 and 113 to heating coil 114 which is wrapped around and secured to the distal portion 107 which extends through the interior of the balloon 103. The heater coil 114 raises the temperature of the inflation fluid within the balloon 103 which in turn raises the temperature of the outside of the balloon. Electrical energy is applied to heater coils to maintain a balloon surface temperature of about 40° to about 120° C. preferably 60°-80° C. while the balloon is inflated. The balloon wall temperature is determined by means of thermocouple 117.

With the balloon 103 inflated, blood is forced to flow through the proximal perfusion port 110 through the second lumen 105 and out the distal perfusion ports 111. Preferably a guidewire 106 is pulled proximally of the perfusion section so that the distal tip is located proximally to at least one of the proximal perfusion ports (preferably all) so as to not interfere with the flow of blood through the second lumen 105. The perfusion of oxygenated blood to locations distal to the catheter avoids a generation of ischemic conditions therein which frequently are already in jeopardy. Furthermore, long term dilations allow for much lower temperatures to be used resulting in less pain and less arterial damage.

The heated inflated balloon of the invention reshapes or remolds, the atherosclerotic plaque, particularly the softer plaques, and generally provides for a much less traumatic dilation of the stenosis. The elevated temperatures over extended periods reduce platelet adhesion, which tends to accelerate restenosis, and the high temperature and pressure can also set the artery wall so as to minimize arterial recoil after the balloon is deflated.

The procedures to dilate a thrombotic occlusion with the catheter assembly in accordance with the invention are essentially the same as that for atherosclerotic plaque, although the maximum pressures are usually much lower when dilating thrombus than when dilating plaque. The time required for dilation is generally inversely related to the balloon temperature. The device is particularly attractive for use in emergency procedures for a myocardial infarction.

The catheter components of the various embodiments of the invention generally can be made of conventional materials. The tubular member may be formed out of extruded polyester tubing and the balloon may be biaxially oriented polyethylene terephthalate materials. The core member of the guidewire may be formed of stainless steel and the helical coil at the distal tip thereof may be formed in whole or in part of stainless steel or more radiopaque materials, such as platinum, palladium, tungsten, rhenium, molybdenum or alloys thereof.

What is claimed is:

1. A balloon dilatation catheter having means to apply heat to atheroma in a patient's artery during the dilatation thereof, comprising:
    a) an elongated tubular member having a first inner lumen extending therein which is adapted to direct inflation fluid therethrough;
    b) a flexible, relatively inelastic balloon on the distal portion of the tubular member which is adapted to receive inflating fluid from the first inner lumen within the tubular member;
    c) a tubular extension having a second inner lumen and extending from the tubular member through the interior of the balloon; and
    d) a resistive or inductive heating means which is disposed around the tubular extension, which has a pair of leads electrically connected to an electrical power source with a frequency of at least 100 kilohertz and which is adapted to heat fluid within the balloon which in turn heats the balloon.

2. The balloon dilatation catheter of claim 1 wherein the tubular extension has at least one perfusion ports distal to the balloon and at least one perfusion port proximal to the balloon which are in fluid communication with the second lumen extending therein whereby oxygenated blood may pass through the balloon and distally to the catheter when the balloon is inflated within a patient's artery.

3. The balloon dilatation catheter of claim 1 wherein the electrical power source has a frequency of about 100 kilohertz to about 100 megahertz.

4. The dilatation catheter of claim 1 wherein the heating element is made of electrically resistive wire and is coiled about the inner member.

5. The dilatation catheter of claim 4 wherein the coiled heating element is bonded to the inner member.

* * * * *